US009107765B2

(12) United States Patent
Ghiselli et al.

(10) Patent No.: US 9,107,765 B2
(45) Date of Patent: Aug. 18, 2015

(54) MEDICAL IMPLANTS WITH INCREASED HYDROPHILICITY

(75) Inventors: Gary Ghiselli, Denver, CO (US); Peter Whang, Milford, CT (US); Jami Hafiz, Minneapolis, MN (US); Joseph Crudden, Hudson, NH (US); Derrick W. Johns, Austin, TX (US)

(73) Assignee: DiFusion Technologies, Inc., Georgetown, TX (US)

( * ) Notice: Subject to any disclaimer, the term of this patent is extended or adjusted under 35 U.S.C. 154(b) by 185 days.

(21) Appl. No.: 13/696,346

(22) PCT Filed: May 6, 2011

(86) PCT No.: PCT/US2011/035468
§ 371 (c)(1),
(2), (4) Date: Nov. 27, 2012

(87) PCT Pub. No.: WO2011/140416
PCT Pub. Date: Nov. 10, 2011

(65) Prior Publication Data
US 2013/0073042 A1  Mar. 21, 2013

Related U.S. Application Data

(60) Provisional application No. 61/332,403, filed on May 7, 2010.

(51) Int. Cl.
| A61F 2/44 | (2006.01) |
| A61L 27/44 | (2006.01) |
| A61L 27/54 | (2006.01) |
| A61F 2/28 | (2006.01) |

(52) U.S. Cl.
CPC .............. *A61F 2/4455* (2013.01); *A61F 2/28* (2013.01); *A61L 27/446* (2013.01); *A61L 27/54* (2013.01); *A61L 2300/404* (2013.01)

(58) Field of Classification Search
CPC ................................ A61F 2/44; A61F 2/4455
USPC ............................ 623/17.11–17.16; 523/113
See application file for complete search history.

(56) References Cited

U.S. PATENT DOCUMENTS

| 4,088,737 A | 5/1978 | Thomas et al. |
| 4,596,574 A | 6/1986 | Urist |
| 4,612,337 A | 9/1986 | Fox, Jr. et al. |
| 4,615,705 A | 10/1986 | Scales et al. |
| 4,775,585 A | 10/1988 | Hagiwara et al. |
| 4,775,586 A | 10/1988 | Bohrn et al. |
| 4,861,808 A | 8/1989 | Billington et al. |
| 4,906,464 A | 3/1990 | Yamamoto et al. |
| 4,911,898 A | 3/1990 | Hagiwara et al. |
| 4,911,899 A | 3/1990 | Hagiwara et al. |
| 4,923,450 A | 5/1990 | Maeda et al. |
| 4,938,955 A | 7/1990 | Niira et al. |
| 4,938,958 A | 7/1990 | Niira et al. |
| 4,957,817 A | 9/1990 | Chau et al. |
| 4,959,268 A | 9/1990 | Hagiwara et al. |
| 5,003,638 A | 4/1991 | Miyake et al. |
| 5,100,671 A | 3/1992 | Maeda et al. |
| 5,151,122 A | 9/1992 | Atsumi et al. |
| 5,180,585 A | 1/1993 | Jacobson et al. |
| 5,192,590 A | 3/1993 | Sherman |
| 5,256,390 A | 10/1993 | Hu |
| 5,266,534 A | 11/1993 | Atsumi et al. |
| 5,294,634 A | 3/1994 | Yamaguchi |
| 5,296,238 A | 3/1994 | Sugiura et al. |
| 5,474,797 A | 12/1995 | Sioshansi et al. |
| 5,478,563 A | 12/1995 | Erami |
| 5,492,763 A | 2/1996 | Barry et al. |
| 5,522,904 A | 6/1996 | Moran et al. |
| 5,556,699 A | 9/1996 | Niira et al. |
| 5,595,750 A | 1/1997 | Jacobson et al. |
| 5,607,464 A | 3/1997 | Trescony et al. |
| 5,609,629 A | 3/1997 | Fearnot et al. |
| 5,614,568 A | 3/1997 | Mawatari et al. |
| 5,647,858 A | 7/1997 | Davidson |
| 5,688,561 A | 11/1997 | Ichikawa et al. |
| 5,709,870 A | 1/1998 | Yoshimura et al. |
| 5,731,087 A | 3/1998 | Fan et al. |

(Continued)

FOREIGN PATENT DOCUMENTS

| BY | 11260 C1 | 10/2008 |
| CA | 2171703 A1 | 4/1995 |

(Continued)

OTHER PUBLICATIONS

European communication mailed Feb. 6, 2014 in co-pending European patent application No. 10759287.5.
Chinese communication, with English translation, issued Jul. 1, 2014 in co-pending Chinese patent application No. 201080062338.X.
Chinese communication, with English translation, issued Jun. 17, 2014 in co-pending Chinese patent application No. CN 201080063584.7.
Chinese communication, with English translation, issued Jul. 7, 2014 in corresponding Chinese patent application No. CN 201180023035.1.
Office Action mailed May 20, 2014 in co-pending U.S. Appl. No. 13/511,176.
Notice of Allowance mailed May 29, 2014 in co-pending U.S. Appl. No. 13/512,702.

(Continued)

*Primary Examiner* — Andrew Yang
(74) *Attorney, Agent, or Firm* — Nields, Lemack & Frame, LLC

(57) ABSTRACT

Devices such as orthopedic implants are composed of a thermoplastic resin such as polyaryletheretherketone (PEEK), and include a ceramic species, such as a zeolite, to enhance its hydrophilic properties. The ceramic species can be a surface coating, can be incorporated or embedded into the thermoplastic resin, or can be both a surface coating and incorporated or embedded into the resin. In certain embodiments, the ceramic species is zeolite that is incorporated into the device, especially at the exposed surface of the device, and is devoid of antimicrobial metal ions. The device is introduced into the body surgically.

10 Claims, No Drawings

(56) References Cited

U.S. PATENT DOCUMENTS

| | | |
|---|---|---|
| 5,753,251 A | 5/1998 | Burrell et al. |
| 5,756,145 A | 5/1998 | Darouiche |
| 5,770,255 A | 6/1998 | Burrell et al. |
| 5,783,570 A | 7/1998 | Yokota et al. |
| 6,015,816 A | 1/2000 | Kostyniak et al. |
| 6,090,732 A | 7/2000 | Ito et al. |
| 6,180,606 B1 | 1/2001 | Chen et al. |
| 6,248,342 B1 | 6/2001 | Trogolo et al. |
| 6,267,590 B1 | 7/2001 | Barry et al. |
| 6,296,863 B1 | 10/2001 | Trogolo et al. |
| 6,436,422 B1 | 8/2002 | Trogolo et al. |
| 6,471,993 B1 | 10/2002 | Shastri et al. |
| 6,582,715 B1 | 6/2003 | Barry et al. |
| 6,585,767 B1 | 7/2003 | Holley et al. |
| 6,720,006 B2 | 4/2004 | Hanke et al. |
| 6,723,428 B1 | 4/2004 | Foss et al. |
| 6,866,859 B2 | 3/2005 | Trogolo et al. |
| 6,946,196 B2 | 9/2005 | Foss |
| 6,984,392 B2 | 1/2006 | Bechert et al. |
| 6,994,883 B2 | 2/2006 | Layrolle et al. |
| 7,270,813 B2 | 9/2007 | Shimp et al. |
| 7,354,605 B2 | 4/2008 | Trogolo et al. |
| 7,357,949 B2 | 4/2008 | Trogolo et al. |
| 8,652,645 B2 | 2/2014 | Dingeldein et al. |
| 8,821,912 B2 | 9/2014 | Crudden et al. |
| 8,840,914 B2 | 9/2014 | Crudden et al. |
| 2002/0099449 A1 | 7/2002 | Speitling |
| 2003/0031687 A1 | 2/2003 | Falder et al. |
| 2004/0109937 A1 | 6/2004 | Jennissen et al. |
| 2005/0058682 A1 | 3/2005 | Sharratt |
| 2005/0064176 A1 | 3/2005 | Terry |
| 2005/0149196 A1 | 7/2005 | Zucherman et al. |
| 2005/0170070 A1 | 8/2005 | Layrolle et al. |
| 2005/0203529 A1 | 9/2005 | Boehm, Jr. et al. |
| 2006/0052479 A1 | 3/2006 | Cougoulic |
| 2006/0069438 A1 | 3/2006 | Zucherman et al. |
| 2006/0161256 A1 | 7/2006 | Ziegler et al. |
| 2006/0177379 A1 | 8/2006 | Asgari |
| 2006/0259020 A1 | 11/2006 | Sharratt |
| 2006/0265065 A1 | 11/2006 | Bagga et al. |
| 2006/0280803 A1 | 12/2006 | Kumar et al. |
| 2007/0015110 A1 | 1/2007 | Zhang et al. |
| 2007/0031515 A1 | 2/2007 | Stucky et al. |
| 2007/0110825 A1 | 5/2007 | Taniguchi et al. |
| 2007/0267029 A1 | 11/2007 | Mason |
| 2007/0276337 A1 | 11/2007 | Trieu |
| 2007/0299472 A1 | 12/2007 | Brighton |
| 2008/0032119 A1 | 2/2008 | Feldhahn et al. |
| 2008/0033572 A1 | 2/2008 | D'Antonio et al. |
| 2008/0063671 A1 | 3/2008 | Morris et al. |
| 2008/0208340 A1 | 8/2008 | Boyd et al. |
| 2008/0249637 A1 | 10/2008 | Asgari |
| 2008/0258337 A1 | 10/2008 | Ajbani et al. |
| 2009/0012612 A1 | 1/2009 | White et al. |
| 2009/0238850 A1 | 9/2009 | Greener |
| 2010/0010632 A1 | 1/2010 | Bourges et al. |
| 2010/0099058 A1 | 4/2010 | Wang |
| 2010/0114317 A1 | 5/2010 | Lambrecht et al. |
| 2010/0215643 A1 | 8/2010 | Clevenger et al. |
| 2011/0022181 A1 | 1/2011 | Kasahara et al. |
| 2012/0141599 A1 | 6/2012 | Johns et al. |
| 2012/0315340 A1 | 12/2012 | Crudden et al. |
| 2012/0323339 A1 | 12/2012 | Olalde Graells et al. |
| 2013/0004585 A1 | 1/2013 | Crudden et al. |
| 2013/0037991 A1 | 2/2013 | Crudden et al. |
| 2014/0366362 A1 | 12/2014 | Crudden et al. |

FOREIGN PATENT DOCUMENTS

| | | | |
|---|---|---|---|
| CN | 1732025 | A | 2/2006 |
| CN | 100360193 | C | 1/2008 |
| CN | 101234304 | A | 8/2008 |
| CN | 101238166 | A | 8/2008 |
| DE | 3228849 | A1 | 2/1984 |
| DE | 10055465 | A1 | 5/2002 |
| EA | 011594 | B1 | 4/2009 |
| EP | 0253663 | A2 | 1/1988 |
| EP | 0722660 | A2 | 7/1996 |
| FR | 2848856 | A1 | 6/2004 |
| JP | 2004-523302 | A | 8/2004 |
| RU | 2313370 | C2 | 12/2007 |
| RU | 2338557 | C2 | 11/2008 |
| WO | 84/01721 | A1 | 5/1984 |
| WO | 99/07326 | A2 | 2/1999 |
| WO | 00/30697 | A1 | 6/2000 |
| WO | 00/32247 | A2 | 6/2000 |
| WO | 00/64505 | A1 | 11/2000 |
| WO | 03/086495 | A1 | 10/2003 |
| WO | 2004/058319 | A1 | 7/2004 |
| WO | 2006/069677 | A2 | 7/2006 |
| WO | 2007/019461 | A2 | 2/2007 |
| WO | 2008/037751 | A2 | 4/2008 |
| WO | 2008/039488 | A2 | 4/2008 |
| WO | 2008/150867 | A2 | 12/2008 |
| WO | 2009/099559 | A2 | 8/2009 |
| WO | 2010/114827 | A1 | 10/2010 |
| WO | 2014/152649 | A1 | 9/2014 |

OTHER PUBLICATIONS

Notice of Allowance mailed Jul. 14, 2014 in co-pending U.S. Appl. No. 13/512,702.

Notice of Allowance mailed Jun. 12, 2014 in co-pending U.S. Appl. No. 13/653,896.

Miscellaneous communication mailed Aug. 6, 2014 in co-pending U.S. Appl. No. 13/653,896.

Supplemental Notice of Allowability mailed Aug. 13, 2014 in co-pending U.S. Appl. No. 13/653,896.

Chinese Communication issued Jan. 6, 2014 in corresponding Chinese patent application No. CN 201180023035.1.

Chinese Communication issued Dec. 3, 2013 in co-pending Chinese patent application No. CN 201080062338.X.

Office Action—Restriction—mailed Jan. 23, 2014 in co-pending U.S. Appl. No. 13/260,571.

Extended European Search Report mailed May 21, 2013 in co-pending European patent application No. EP 10833925.0.

Biomaterials, vol. 28, 2007, pp. 4845-4869, "PEEK biomaterials in trauma, orthopedic, and spinal implants", Kurtz, et al.

Office Action mailed Jan. 10, 2013 in co-pending U.S. Appl. No. 13/511,176.

Office Action mailed Jan. 10, 2013 in co-pending U.S. Appl. No. 13/512,702.

Russian communication dated Apr. 14, 2014 in co-pending Russian patent application No. 2011144020/15(066044).

Russian communication dated Apr. 17, 2014 in co-pending Russian patent application No. 2012129171/15(045686).

Canadian communication dated Apr. 9, 2014 in corresponding Canadian patent application No. 2,795,836.

Journal of the Physical Society of Japan, vol. 77, No. 6, Jun. 2008, 064712, "Photoluminescence of the Dehydrated Ag-type Zeolite A Packed under Air", pp. 064712-1-064712-7, Hoshino, et al.

National Institute of Standards and Technology (NIST) recommended practice guide, Special Publication 960-17, Sep. 2006, "Porosity and Specific Surface Area Measurements for Solid Materials", 91 pages, Klobes, et al.

J. Phys. Chem. A, 2000, vol. 104, pp. 7473-7483, "Colors of Ag+-Exchanged Zeolite A.", Seifert, et al.

Office Action mailed May 12, 2014 in co-pending U.S. Appl. No. 13/260,571.

European Communication mailed Aug. 27, 2013 in co-pending European patent application No. EP 10836743.4.

Medical Design Technology Online, Jan. 28, 2010, 5 pages, http://www.mdtmag.com/scripts/ShowPR.asp?PUBCODE=046&ACCT=0006305&ISSUE . . . , "Taking a Peek at Material Options for Orthopedics", Kinbrum.

International Search Report/Written Opinion mailed May 13, 2010 in co-pending PCT applicaiton No. PCT/US 10/29180.

International Preliminary Report on Patentability dated Dec. 6, 2011 in co-pending PCT application No. PCT/US 10/29180.

(56) References Cited

OTHER PUBLICATIONS

Russian Communication, with English translation, issued Oct. 9, 2013 in co-pending Russian patent applicaiton No. RU 2011144020.
"Antimicrobial Efficacy of a novel Orthobiologic PEEK in treating Surgical Site Spine Infections", http://www.difusiontech.com/wp-contentJuploads/NASS-Summer-Conference_2013-Abstract_final2.pdf, NASS Summer Session, Aug. 2-5, 2013, Naples, FL, 2 pages, Eastlack, et al.
Rothman-Simeone—The Spine, 6th Edition, vol. II, Chapter 98, Garfin S., ed., "Postoperative Spinal Infections", 53 pages, Smith, et al.
International Search Report and Written Opinion mailed Aug. 25, 2011 in co-pending PCT application No. PCT/US2010/059868.
International Preliminary Report on Patentability mailed Jun. 21, 2012 in co-pending PCT application No. PCT/US2010/059868.
International Search Report and Written Opinion mailed Aug. 19, 2011 on co-pending PCT application No. PCT/US2010/058009.
International Preliminary Report on Patentability mailed Jun. 7, 2012 in co-pending PCT application No. PCT/US2010/058009.
International Search Report and Written Opinion mailed Jan. 9, 2012 in corresponding PCT application No. PCT/US2011/035468.
International Preliminary Report on Patentability mailed Aug. 7, 2012 in corresponding PCT application No. PCT/US2011/035468.
Neurosurg. Focus, vol. 10, No. 4, 2001, 7 pages, "Bone Graft Substitutes for the Promotion of Spinal Arthrodesis", Helm, et al.
Chinese communication, with English translation, mailed Sep. 30, 2014 in co-pending Chinese patent application No. 201080062338.X.
Final Rejection mailed Oct. 16, 2014 in co-pending U.S. Appl. No. 13/260,541.
Final Rejection mailed Jan. 5, 2015 in co-pending U.S. Appl. No. 13/511,176.
Russian Communication, with English translation, issued Jan. 12, 2015 in co-pending Russian patent application 2012126078/15(040280).
Russian communication, with English translation, dated Sep. 15, 2014 in co-pending Russian patent application No. 2012126078/15(040280).
Office Action mailed Oct. 8, 2014 in co-pending U.S. Appl. No. 14/471,329.
Zinc Toxicity in Humans, 2007, Elsevier B.V. publication, pp. 1-7, Jerome NRIAGU, School of Public Health, University of Michigan.
Chinese communication, with English translation, mailed Mar. 30, 2015 in corresponding Chinese patent application No. 201180023035.1.
International Search Report and Written Opinion mailed Jul. 21, 2014 in co-pending PCT application No. PCT/US14/27576.
International Preliminary Report on Patentability mailed Apr. 8, 2015 in co-pending PCT application No. PCT/US14/27576.
Journal of the Brazilian Chemical Society, vol. 19, No. 1, Sao Paolo, 2008, pp. 1-11, downloaded from the interenet Mar. 1, 2013, "Preparation and characterization of poly(ether ether ketone) derivatives", Conceicao, et al.
Net Motion, Inc., copyright 2003, http://www.netmotion.com/htm_files/wh_properties.htm#chem, pp. 1-8, downloaded from internet Mar. 1, 2013, All you want to know about Polyetheretherketone (PEEK), Chemical Resistance of PEEK, PEEK and Polymer chemical resistance.
VICI AG International, 2013, VICI JOUR-Technical Support, Chemical Resistance of Peek and Other Polymers, Chart displaying Peek and Polymer Chemical Resistance, 3 pages.
The Structure and Synthesis of Zeolite Molecular Sieves, Jilin University Press, Aug. 1987, 1st Edition, pp. 6 and 8, 4 pages, Xu, et al.
Office Action mailed Apr. 22, 2015 in co-pending U.S. Appl. No. 13/260,571.
Notice of Allowance mailed Mar. 26, 2015 in co-pending U.S. Appl. No. 14/471,329.
European Communication mailed Aug. 27, 2013 in co-pending European patent application No. EP 10836743A.
English translation of Chinese Communication issued Oct. 30, 2013 in co-pending Chinese patent application No. CN 201080063584.7.
Russian Communication, with English translation, issued Nov. 20, 2013 in co-pending Russian patent application No. RU 2012129171.
European Communication mailed Sep. 4, 2013 in corresponding European patent application No. EP 11778401.7.
Antimicrobial Agents and Chemotherapy, Dec. 2005, vol. 49, No. 12, p. 4853-4859, "Role of Silver Ions in Destabilization of Intermolecular Adhesion Forces Measured by Atomic Force Microscopy in *Staphylococcus epidermidis* Biofilms", Chaw, et al.
Clinical Microbiology Reviews, Apr. 2002, vol. 15, No. 2, pp. 155-166, Focus, "Bacterial Adhesion: Seen Any Good Biofilms Lately?", Dunne, Jr., et al.
J Bone Miner Res., Nov. 1992, vol. 7(11), pp. 1281-1289, 1 page Abstract, http://www.ncbi.nlm.nih.gov/pubmed/1334616, "Zeolite A increases proliferation, differentiation, and transforming growth factor beta production in normal adult human osteoblast-like cells in vitro", Keeting, et al.
Medical Design Technology Online, Jan. 28, 2010, 5 pages, http://www.mdtmag.conniscripts/ShowPR.asp? PUBCODE=046&ACCT=0006305&ISSUE . . . , "Taking a PEEK at Material Options for Orthopedics", Kinbrum.
Journal of Polymer Science: Part B: Polymer Physics, 2004, vol. 42, pp. 1548-1563, "Poly(ether ether ketone)/Polyy (aryl ether sulfone) Blends: Melt Rheological Behavior", Nandan, et al.
Final Rejection mailed Oct. 23, 2013 in co-pending U.S. Appl. No. 13/511,176.
Final Rejection mailed Jul. 17, 2013 in co-pending U.S. Appl. No. 13/512,702.
Office Action mailed Dec. 11, 2013 in co-pending U.S. Appl. No. 13/653,896.
International Search Report/Written Opinion mailed May 13, 2010 in co-pending PCT application No. PCT/US 10/29180.
International Preliminary Report on Patentability dated Dec. 6, 2011 in co-pending PCT application No. PCT/US10/29180.
Chinese Communication issued Sep. 26, 2012 in co-pending Chinese patent application No. CN 201080015851.3.
Russian Communication, with English translation, issued Oct. 9, 2013 in co-pending Russian patent application No. RU 2011144020.
DiFusion Technologies research paper, created Oct. 14, 2013, "Novel Orthopedic Implant Material Protects Osteoblast Viability in the Presence of Biofilm-Forming MRSA", 4 pages.
Emerging Infectious Diseases, vol. 7, No. 2, Mar.-Apr. 2001, pp. 277-281, "Biofilms and Device-Associated Infections", Donlan.
"Antimicrobial Efficacy of a novel Orthobiologic PEEK in treating Surgical Site Spine Infections", http://www. difusiontech.com/wp-content/uploads/NASS-Summer-Conference_2013-Abstract_final2.pdf, NASS Summer Session, Aug. 2-5, 2013, Naples, FL, 2 pages, Eastlack, et al.
"Exploring the efficacy of a self-sterilizing orthobiologic PEEK as a viable biomaterial for spinal surgery", http://www.nassannualmeeting.org/Documents/AMB_FinalProgram.pdf, Abstract, NASS Annual Meeting, Oct. 9-12, 2013 NewOrleans, LA, 3 pages, Eastlack, et al.
The Journal of Biological Chemistry, vol. 263, No. 13, May 5, 1988, pp. 6276-6280, "Regulation of the Enterotoxin B Gene in *Staphylococcus aureus*", Gaskill, et al.
Ann Nutr Metab., 1993, 37(5):245-252, 2 page abstract, "Impaired mechanical strength of bone in experimental copper deficiency", Jonas, et al.
European Cells and Materials, vol. 8, 2004, pp. 37-57, "Concise Review of Mechanisms of Bacterial Adhesion to Biomaterials and of Techniques Used in Estimating Bacteria-Material Interactions", Katsikogianni, et al.
Clin. Orthop. Relat. Res., Nov.-Dec. 1981, vol. 161, pp. 154-162, 1 page Abstract, "Antibacterial and osteoinductive properties of demineralized bone matrix treated with silver", Kramer, et al.
Medicaldevice-network.com, Jul. 2011, http://www.medicaldevice-network.com/features/feature128303, "Peek performance: a next-generation biomaterial", 5 pages, Kurtz.

(56) References Cited

OTHER PUBLICATIONS

The Journal of Nutrition, 2002, http://jn.nutrition.org/content/132/1013135.full.pdf+html, Nutrient Requirements, "Bone Morphology, Strength and Density Are Compromised in Iron-Deficient Rats and Exacerbated by Calcium Restriction", pp. 3135-3141, Medeiros, et al.

BMC Musculoskeletal Disorders, 2013, 14:187, http://www.biomedcentral.com/1471-2474/14/187, 11 pages, "*Staphylococcus aureus* biofilms decrease osteoblast viability, inhibits osteogenic differentiation, and increases bone resorption in vitro", Sanchez, Jr., et al.

United States Environmental Protection Agency, Silver-Copper Zeolite Data Review, Feb. 15, 1994, 3 pages.

Mexican communication, with English translation, dated Apr. 17, 2015 in corresponding Mexican patent application No. MX/a/2012/012710.

Russian communication, with English translation, dated Jun. 3, 2015 in corresponding Russian patent application No. 2012152640.

"Opisanie tseolita i ego svoystv", Aug. 4, 2004, https://web.archive.org/web120040804124452/http://www.ceolit.smila.com/op.htm 04.08.2004, 3 pages.

MEDICAL IMPLANTS WITH INCREASED HYDROPHILICITY

This application claims priority of U.S. Provisional Application Ser. No. 61/332,403 filed May 7, 2010, the disclosure of which is incorporated herein by reference.

BACKGROUND

Implantable medical devices are implanted into the body for various reasons including orthopedic applications (e.g., hip replacement, spinal procedures, knee replacement, bone fracture repair, etc). In view of the structural integrity required by such devices, materials of fabrication are limited and generally consist of metal, plastic and composites.

The benefits derived from these devices are often offset by infection which in some cases can lead to sepsis and death. The most common organisms causing infections are *Staphylococcus epidermidis* and *Staphylococcus aureus*. *Staphylococcus epidermidis* is a major component of the normal bacterial flora of human skin and mucous membranes. It is a common pathogen that often colonizes patients in hospital settings who have surgical implants due to the microbes' ability to adhere to medical devices and form a biofilm. Additionally, methicillin-resistant *Staphylococcus aureus* (MRSA) is a type of staphylococcus bacteria that is resistant to many antibiotics is therefore of particular concern. Other gram-positive bacteria, gram-negative bacteria and fungal organisms also are causative organisms that may be problematic.

As microorganisms come in close proximity to the surface of the medical device, they will either be attracted or repelled by it depending on the sum of the different non-specific interactions. In biological systems, hydrophobic/hydrophilic interactions play an important role in the pathogenesis of a wide range of microbial infections.

Many bacteria can form multicellular coatings, or biofilms, on bioengineered implants. Biofilms facilitate the proliferation and transmission of microorganisms by providing a stable and protective environment for their growth. These biofilms may often result in a broad systemic infection.

In many instances, when implants are seeded by organisms which are protected by tenacious biofilms, the implant must be removed and the patient must be treated with a prolonged course of one or more antibiotics in an effort to cure the infection, after which time a new implant is then reimplanted. This process not only subjects the patient to additional trauma and pain but is also extremely expensive.

Not surprising, a great deal of research has been devoted toward preventing the colonization of the surfaces of orthopedic implants by bacterial and fungal organisms with the use of antimicrobial agents such as antibiotics which may be bound to the surface of these devices.

Thermoplastic resins including polyetherketoneketone (PEKK) and polyetheretherketone (PEEK) have been found to be a useful material for these implants. PEEK is particularly suitable because its modulus of elasticity closely matches that of bone. However, PEEK is a hydrophobic material and bacteria tend to adhere easily to these types of surfaces. It is also an organic material which does not carry significant surface charges. Consequently, it may be desirable to develop a medical implant composed of one or more thermoplastic resins that has reduced hydrophobic properties, and/or that has a net negative charge, particularly at an exposed surface when implanted.

SUMMARY

The shortcomings of the prior art have been overcome by the embodiments disclosed herein, which relate to devices, such as structural orthobiologic materials, particularly intracorporeal devices such as surgical implants, more particularly orthopedic implants, even more particularly spinal implants. In certain embodiments, the device is osteoconductive and is comprised of a thermoplastic resin such as polyaryletheretherketone (PEEK) or polyetherketoneketone (PEKK), and includes a ceramic species, such as a zeolite, to add hydrophilicity and/or a negative charge to the resin. The ceramic species is devoid of antimicrobial metal ions such as silver, copper, zinc, mercury, tin, lead, gold, bismuth, cadmium, chromium and thallium ions. The ceramic species can be a surface coating, can be incorporated or embedded into the thermoplastic resin, or can be both a surface coating and incorporated or embedded into the resin.

In certain embodiments, the ceramic species is zeolite that is incorporated into the device, especially at the exposed surface of the device. The device is introduced into the body surgically. Radio opacity when viewed under X-ray is retained.

DETAILED DESCRIPTION

Embodiments disclosed herein relate to the use of ceramics in combination with medical implants comprising thermoplastic resins such as PEEK, PEKK or the like to alter the hydrophobicity of the polymer and impart a negative charge to the polymer such as at an exposed surface of the polymer, in order to minimize or eliminate biofilm formation, and/or to disrupt the integrity of the biofilm and thus its ability to protect bacteria.

Although the present inventors do not intend to be bound to any particular theory of operation, it is believed that biofilms develop because bacteria attach to the implant. The hydrophobic properties of the implant (now with attached bacteria) prevent antimicrobials from attacking the biofilm containing bacteria. The PEEK/zeolite combination with ionic properties, increases the ability of antimicrobial moieties to permeate in and kill the bacterial pathogen rather than be repelled by the hydrophobic surface properties of naked PEEK.

All bacteria adhere better to hydrophobic surfaces, and it also may be more difficult to detach bacteria from hydrophobic surfaces.

The first stage of bone formation is protein adsorption. Typically, proteins that are most important (i.e., RGD peptide) for bone forming cells attach to surfaces that are negatively charged. Additionally, the charged surface allows the proteins to attach in the correct conformation, leading to the attachment of an optimal number of proteins. The Second stage of bone formation is the attachment of pre-osteoblast cells to the adsorped proteins. These cells then form mature osteoblasts, spread phyllopodia and start the osteoblast maturation/proliferation process. Mature osteoblasts produce ECM (extra cellular matrix) which in combination with the cells, mineralizes into woven bone. PEEK is highly hydrophobic which prevents protein adsorption without which the bone forming process cannot start. By incorporating zeolite into the PEEK structure, a negatively charged surface is created which has the potential to initiate the protein adsorption process.

In addition, tissue does not adhere well to pure PEEK; the tissue simply grows up against the PEEK and forms an interface with minimal adhesion between the two materials. This interface provides an area which is very susceptible to formation of bacterial biofilms, even from systemic bacteria which arrive long after surgery. Since the hydrophilic nature and/or charges on the surface of composite of PEEK and ceramics such as zeolite will foster the growth and adhesion of fibroblasts and osteoblasts that interact with developing tissue, the interface will disappear soon after surgery and the potential for biofilm there will be greatly reduced or even eliminated.

In certain embodiments, the device is configured for use in spinal fusion (arthrodesis) which is often employed to stabilize an unstable spinal column due to structural deformity, trauma, degeneration, etc. Fusion is a surgical technique in which one or more vertebrae of the spine are united together ("fused") to reduce or eliminate relative motion between them or to fix the spatial relationship between them. Spinal fusions include posterolateral fusion, posterior lumbar interbody fusion, anterior lumbar interbody fusion, anterior/posterior spinal fusion, cervical fusion, thoracic fusion and interlaminar fusion. In certain embodiments, the devices are for insertion in an intervertebral space between adjacent vertebrae. In certain embodiments, a fusion site is identified between adjacent vertebrae and a bone graft is implanted at said site. In certain embodiments, the implant is a spinal interbody cage, including cages comprising titanium, carbon fibers, biocompatible materials such as polyetheretherketone (PEEK), polyetherketoneketone (PEKK), or other synthetic substances. In certain embodiments, zeolite particles are incorporated into the PEEK interbody cage. In certain embodiments, the cage is loaded with osteoconductive and/or osteoinductive agents to promote fusion. Preferably, ceramic particles are incorporated into the resin such that a negative charge is imparted to an exposed surface of the resin. The term "exposed surface" is intended to include one or more surfaces of an implantable device that when implanted, is exposed to or in contact with body tissue and/or fluids.

Either natural zeolites or synthetic zeolites can be used to make the zeolites used in the embodiments disclosed herein. "Zeolite" is an aluminosilicate having a three dimensional skeletal structure that is represented by the formula: $XM_{2/n}O.Al_2O_3.YsiO_2.ZH_2O$, wherein M represents an ion-exchangeable ion, generally a monovalent or divalent metal ion, n represents the atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, socialite, mordenite, analcite, clinoptilolite, chabazite and erionite.

Zeolites can be obtained in master batches of pellets of low density polyethylene, polypropylene, ultra high molecular weight polyethylene or polystyrene, containing suitable amounts of zeolite particles, usually 20 wt. % of zeolite particles. When provided in this form, the pellets of resin containing the zeolite particles can be easily mixed with resins used to make the implants or used to make coatings to be applied to the implants, as set forth in U.S. Pat. No. 6,582,715, the disclosure of which is hereby incorporated by reference. Typical amounts of zeolite particles incorporated in an implant resin range from 0.01 to 10 wt. %, more preferably 0.01 to 8.0 wt. %, most preferably 0.1 to 5.0 wt. %. The method used to coat or otherwise incorporate the ceramic into the resin is not particularly limited, and can include spraying, painting or dipping. When compounded into PEEK, for example, the PEEK should be protected from sources of moisture and contamination. The compounding can be carried out by blending. The ceramic species can be a surface coating, can be incorporated or embedded into the thermoplastic resin, or can be both a surface coating and incorporated or embedded into the resin.

Other suitable resins include low density polyethylene, polypropylene, ultra high molecular weight polyethylene or polystyrene, polyvinyl chloride, ABS resins, silicones, rubber, and mixtures thereof. These can be formulated to contain suitable amounts of zeolite particles, usually about 20 wt. %. An UHMWPE is preferred for the implant devices.

The masterbatch is a concentrated mixture of pigments and/or additives (e.g., zeolite powder) encapsulated during a heat process into a carrier resin which is then cooled and cut into a granular shape. Using a masterbatch allows the processor to introduce additives to raw polymer (let down resin) economically and simply during the plastics manufacturing process.

The zeolite incorporated into the resin and implanted is devoid of antimicrobial metal ions.

Under conditions of high temperature and high shear, the zeolite is incorporated into the resin, such as by mixing doped metal zeolites into molten PEEK (melting point between 300 and 400° C.), followed by molding and processing of the composite blend.

Example

About 5% by weight of the zeolite powder is mixed thoroughly with the powdered or prilled PEEK. The mixture is brought up to temperature and processed at 400° C. using high shear. The zeolite and PEEK must be dry before processing in order to minimize decomposition and void formation in the product.

The material can be formed into prills for further processing, cast into blocks, extruded into rods or injection molded into the final desired shapes.

The block and rod materials can be machined into shapes which are suitable for use as orthopedic implants or other designs where antimicrobial PEEK finds application. Implants can be designed to provide enhanced surface area by having grooves cut in the surfaces or by producing products with holes in the body of the pieces. Surface area can be further enhanced by sanding or abrasive blasting of the surfaces.

What is claimed is:

1. A medical implant having an exposed surface, said implant comprising a thermoplastic resin having aluminosilicate particles incorporated therein, said aluminosilicate particles being devoid of antimicrobial metal ions and being present in said resin in an amount sufficient to impart a negative charge to said exposed surface of said implant.

2. The implant of claim 1, where said implant is an interbody spinal cage.

3. The implant of claim 1, wherein said thermoplastic resin comprises PEEK.

4. The implant of claim 1, wherein said aluminosilicate is represented by the formula $XM_{2/n}O.Al_2O_3.YsiO_2.ZH_2O$ wherein M represents an ion-exchangeable ion, n represents the atomic valency of the (metal) ion, X and Y represent coefficients of metal oxide and silica respectively, and Z represents the number of water of crystallization.

5. A method of minimizing biofilm formation in a patient, comprising implanting in said patient a device having an exposed surface, said device comprising a thermoplastic resin having aluminosilicate particles incorporated therein, said aluminosilicate particles being devoid of antimicrobial metal ions and being present in said resin in an amount sufficient to impart a negative charge to said exposed surface of said device.

6. The method of claim 5, wherein said aluminosilicate is represented by the formula $XM_{2/n}O.Al_2O_3.YsiO_2.ZH_2O$ wherein M represents an ion-exchangeable ion, n represents the atomic valency of the (metal) ion, X and Y represent coefficients of metal oxide and silica respectively, and Z represents the number of water of crystallization.

7. A medical implant having an exposed surface, said implant comprising a thermoplastic resin having aluminosilicate particles incorporated therein, said aluminosilicate particles being devoid of antimicrobial metal ions, wherein said aluminosilicate particles are present in an amount effective for rendering said exposed surface hydrophilic.

8. The implant of claim 7, wherein said thermoplastic resin comprises PEEK.

9. The implant of claim 7, wherein said implant is an interbody spinal cage.

10. The implant of claim 7, wherein said aluminosilicate is represented by the formula $XM_{2/n}O \cdot Al_2O_3 \cdot YsiO_2 \cdot ZH_2O$ wherein M represents an ion-exchangeable ion, n represents the atomic valency of the (metal) ion, X and Y represent coefficients of metal oxide and silica respectively, and Z represents the number of water of crystallization.

* * * * *